United States Patent [19]
Callan et al.

[11] Patent Number: 6,007,333
[45] Date of Patent: Dec. 28, 1999

[54] ENDOSCOPIC METHOD AND DEVICE FOR SUBGINGIVAL DENTAL PROCEDURES

[75] Inventors: Donald P. Callan, Little Rock, Ark.; Wendell Victor Ebling, Lake Forest, Calif.; Ronald Bruce Beckman, Mission Viejo, Calif.; James Charles Elmore, Mission Viejo, Calif.; Craig Gordon Edwards, Mission Viejo, Calif.

[73] Assignee: International Bioview, Inc., Irvine, Calif.

[21] Appl. No.: 09/151,466

[22] Filed: Sep. 11, 1998

[51] Int. Cl.⁶ ........................................ A61C 1/00
[52] U.S. Cl. .............................. 433/29; 433/143
[58] Field of Search ............................ 433/29, 143, 118, 433/119, 122, 123, 124, 120

[56] References Cited

U.S. PATENT DOCUMENTS

| | | | |
|---|---|---|---|
| 4,915,626 | 4/1990 | Lemmey | 433/29 |
| 5,052,924 | 10/1991 | Berg | 433/29 |
| 5,230,621 | 7/1993 | Jacoby | 433/29 |
| 5,328,365 | 7/1994 | Jacoby . | |
| 5,429,502 | 7/1995 | Cooper et al. | 433/29 |
| 5,634,790 | 6/1997 | Pathmanabhan et al. | 433/29 |

*Primary Examiner*—Jeffrey A. Smith
*Assistant Examiner*—Eduardo C. Robert
*Attorney, Agent, or Firm*—Stetina Brunda Garred & Brucker

[57] ABSTRACT

An improved endoscopic system for visualizing subgingival dental procedures. The device comprises a dilator projection incorporated into or onto the body of a dental instrument utilized to remove plaque and calculus from subgingival tooth surfaces. The projection preferably comprises a thin, flat shield portion having an arcuate shank portion extending therefrom. In use, the shield portion of the dilator projection is operative to dilate or spread the gingiva away from the adjacent tooth surfaces upon which the dental instrument is utilized to remove plaque and calculus. Formed within the shank portion of the dilator projection is at least one lumen for receiving an endoscopic viewing apparatus, that receives and transmits an optical image from the interior of the gingival sulcus or periodontal pocket to an image displaying device positioned outside the patient's body. Additional lumens may be formed within the shank portion of the dilator projection for the infusion of fluid or suction/aspiration.

21 Claims, 4 Drawing Sheets

ENDOSCOPIC METHOD AND DEVICE FOR SUBGINGIVAL DENTAL PROCEDURES

FIELD OF THE INVENTION

The present invention relates generally to dental equipment, and more particularly, improved apparatus for permitting visualization, guidance, monitoring and/or assessment of any type of treatment procedure directed to subgingival tooth services or parodontium, including, but not limited to, subgingival plaque and calculus removal procedures.

BACKGROUND OF THE INVENTION

Periodontal disease encompasses a group of different disorders which affect the gums or supporting structures of the teeth. The general epidemiology of plague associated periodontal disease typically begins with the formation of supragingival microbial plaque which, if left untreated, subsequently invades the normally closed space between the free gingiva and the tooth surface. If left unremoved, such subgingival plaque gives rise to the formation of harden calculi and areas of erosion on the subgingival surfaces of the tooth (i.e., the subgingival enamel and root surfaces). Resultant inflammation of the surrounding tissues and recession of the surrounding connective tissue and bone then occurs. Such inflammation and recession of the periodontia results in the formation of a gap or "periodontal pocket" between the gingival tissue and the adjacent tooth surface. The gradual loss of ligamentous attachment and surrounding alveolar bone mass in periodontal disease often results in loss of the affected tooth, unless effective treatment is administered to halt the progression of the disease.

Clinically, plaque associated periodontal disease may be treated by either a surgical or nonsurgical approach. The surgical approach to the treatment of plaque associated periodontal disease typically involves the performance of one or more surgical procedures whereby the gingival tissue is excised and the underlying tooth surfaces (e.g., subgingival enamel and a portion of the root) are visually examined and subjected to scaling and root planning under direct visualization. Although the surgical approach to the treatment of plaque associated periodontal disease is often highly effective, such surgical approach is also associated with significant expense and a significant degree of patient discomfort.

The nonsurgical approach to the treatment of plaque associated periodontal disease typically involves procedures known as subgingival scaling and root planing. Some chemical formulations for dissolving and/or removing subgingival plaque and/or calculus are also known. Subgingival scaling and root planing procedures are typically accomplished by inserting a hand instrument, an ultrasonic or sonic cleaning device and/or a rotating instrument into the periodontal pocket (PP), without cutting or excising the gingiva, for the purpose of scraping plaque or dental calculus from the subgingival tooth surfaces. Typically, such instruments are comprised of an elongate handle portion having a working part or treatment head or tip, the latter being operative to remove the target plaque and/or calculus. The ultimate effectiveness of such subgingival scaling and root planing procedures, or chemical plaque/calculus removal methods, is dependent upon the completeness with which removal of plaque or calculi has been effected by such procedures.

Because the surrounding gingiva remain intact, the operator is unable to directly view the subgingival tooth surfaces when carrying out such subgingival plaque and calculus removal procedures. The inability to visualize the subgingival tooth surfaces make it virtually impossible for the aperture to ascertain whether all of the subgingival plaque or calculus has been effectively removed. Failure to completely remove all subgingival deposits of plaque or dental calculus may result in progression of the periodontal disease. Such progression of the disease often necessitates abandonment of the nonsurgical treatment approach in favor or the more costly and painful surgical approach.

In an attempt to address the need for new devices and techniques whereby the subgingival tooth surface may be endoscopically viewed to permit visual assessment and/or guidance of subgingival plaque/calculus removal procedures without the need for surgical cutting or excision of the gums, there is disclosed in U.S. Pat. Nos. 5,230,621 and 5,328,365 entitled, respectively, Endoscopic Method And Device For Subgingival Dental Procedures And System; and Method For Endoscopic Subqingival Dental Procedures (both to Jacoby), endoscopic viewing devices which are insertable into the subgingival sulcus periodontal pocket to enable the operator to view the subgingival tissue and/or tooth surfaces, without the need for surgical incision or cutting of the gingiva, the teachings of which are expressly incorporated herein by reference. Specifically, there is provided an optical head formed upon the dental hand instrument that is aimed or positioned toward the leading edge of the working part or blade of such hand instrument to permit the operator to endoscopically view the plaque and/or calculus removal being effected by the leading edge of the working part or blade of the instrument. Each of the aforementioned Patents further disclose dental instrumentation optionally incorporating as a part thereof a dilator projection that is sized and configured to spread and hold the gingiva away from the tooth surface over a region or area of approximately several square centimeters ahead of the working part or blade of a hand instrument used for scaling and root planing.

Notwithstanding the general effectiveness of those devices disclosed in U.S. Pat. Nos. 5,230,621 and 5,328,365, such prior art devices suffer from significant drawbacks. In this regard, such systems produce a limited field of vision and depth of view based upon the proximity of the optical head relative the dilator projection and/or working part or blade of the instrument. Specifically, the visual image generated by the optical head provides the dentist or hygienist with a substantially limited view of the surface of the tooth sought to be visualized. In fact, due to the orientation of the optical head pursuant to the teachings of the aforementioned patents, the working part of the instrument becomes the dominant object viewed thereby, often consuming virtually all of the field of vision. As a result, the dentist or hygienist is therefore limited in his or her ability to directly visualize the subgingival tooth surface sought to be endoscopically viewed.

Accordingly, there is a substantial need in the art for improved devices and techniques whereby the subgingival tooth surfaces may be endoscopically viewed to a much greater extent than prior art devices to thus permit visual assessment and/or guidance of subgingival plaque/calculus removal via non-surgical procedures.

SUMMARY OF THE INVENTION

The present invention specifically addresses and alleviates the above-identified deficiencies in the art. In this regard, the present invention is directed to a dilator projection having an endoscopic viewing apparatus formed therewithin that, when used in combination with an instrument utilized to remove plaque and calculus from subgingival tooth surfaces, provides the operator thereof with a substantially greater field of vision and depth of vision of subgingival tooth surfaces than prior devices. Advantageously, the projection may be incorporated into or onto the body of any of a variety of conventional dental instruments to remove plaque and calculus from subgingival tooth surfaces, which include, but are not limited to, hand instruments, sonic instruments, ultra-sonic instruments, and/or rotating instruments.

The projection preferably comprises a thin, flat shield having an arcuate arm or shank portion extending therefrom. The elongate shank portion is attached or formed upon the instrument such that the same extends forward toward the distal end of the instrument such that the shield portion of the projection mates and cooperates with the working part or blade of such instrument. In use, the shield portion of the projection serves to dilate or spread the gingival away from the adjacent tooth surfaces from which the blade or working part removes deposits of plaque or calculus.

At least one lumen is formed along the link of the shank portion, which defines at least one aperture at the distal-most end thereof at the juncture between the shank and the shield portion of the projection. The lumen and aperture formed thereby are designed to receive an endoscopic viewing apparatus, the latter of which preferably comprises a bundle of optical fibers which extend through the lumen and terminate distally in an optical viewing/illumination head.

Advantageously, the lumen formed within the shank portion of the projection, and more particularly the aperture formed at the distal-most end thereof, serves to selectively cant or tilt the optical head formed at the distal-most end of the endoscope viewing apparatus such that the field of vision of the subject tooth surfaces upon which the plaque removal procedure is performed is maximized. The position and orientation of the optical head further increases the depth of vision of prior art devices insofar as the optical head is situation further back and across from the working part or blade of the instrument utilized to remove the plaque or calculus. In further refinements of the invention, the shank portion of the projection may be provided with additional lumens for performing additional functions inherent in the removal of plaque and/or calculus. For example, an optional infusion fluid outlet port as well as an optional suctional aspiration port may be provided.

It is therefore an object of the present invention to provide a dilator projection having an endoscopic viewing apparatus formed thereon for use with a dental instrument for removing plaque and calculus from subgingival tooth surfaces that provides the operator thereof with a substantially greater field of vision and depth of vision of the subgingival tooth surfaces than prior art devices.

Another object of the present invention is to provide a dilator projection having an endoscopic viewing apparatus formed thereon that may be incorporated into any of a variety of conventional dental instruments utilized to remove plaque and calculus from subgingival tooth surfaces including, but not limited to, hand instruments, sonic instruments, ultra-sonic instruments, and/or rotating instruments.

Another object of the present invention is to provide a dilator projection having an endoscopic viewing apparatus formed thereon wherein the dilator projection thereof is effected to spread and hold the gingival away from the tooth surface upon which the working part or blade of the dental instrument is operative to remove plaque and/or calculus and further does not interfere with the ability of the endoscopic viewing apparatus formed thereon to provide enhanced visualization of the subject tooth surface.

Still further of the present invention is to provide a dilator projection having an endoscopic viewing apparatus formed thereon wherein the dilator projection thereof that is of simple, durable construction, may be readily incorporated into or onto existing dental instrumentation, is relatively inexpensive to manufacture, and, in addition to providing enhanced visualization of subgingival tooth surfaces, may be further modified to perform other utility functions, such as fluid infusion and suction or aspiration.

BRIEF DESCRIPTION OF THE DRAWINGS

These, as well as other features of the present invention will become more apparent upon reference to the drawings wherein:

FIG. 1b is a schematic diagram of a portion of the human periodontal anatomy exhibiting the effects of plague associated with periodontal disease;

FIG. 3a' is an enlarged frontal perspective view of the distal portion of the instrument and gingival tissue dilator projection with viewing apparatus shown in FIG. 3;

DETAILED DESCRIPTION OF THE PREFERRED EMBODIMENTS

The following detailed description and accompanying drawings are provided for purposes of illustrating and describing presently preferred embodiments of the invention and are not intended to limit the scope of the invention in anyway.

Figures 1, 1A, 2, 2A:
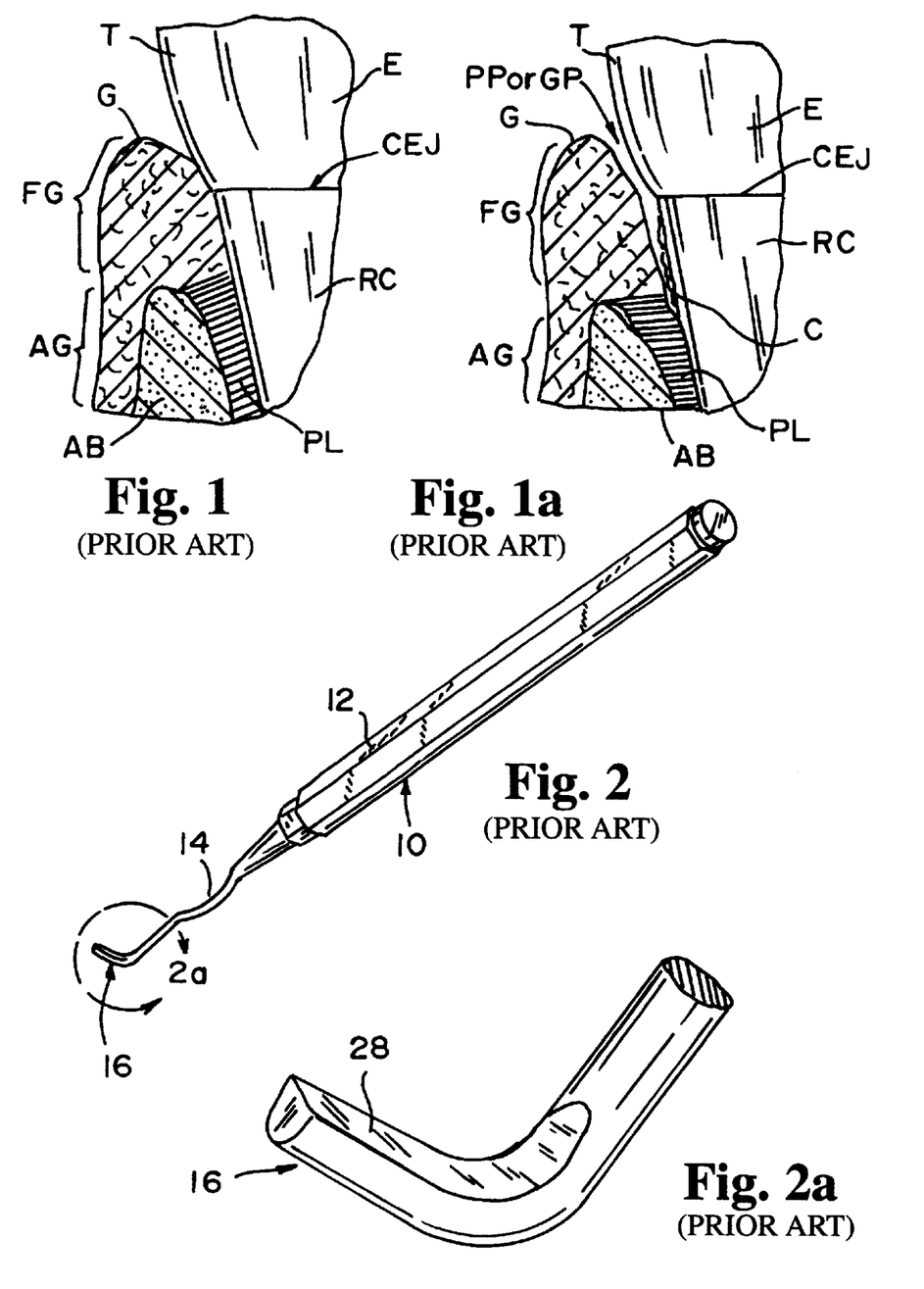
FIG. 1a is a schematic diagram of a portion of the normal human periodontal anatomy.
FIG. 2 is a perspective view of a prior art subgingival hand curette instrument.
FIG. 2a is an enlarged view of the distal shank and working part portions of the instrument shown in FIG. 2.

FIG. 1a shows the normal, undiseased periodontal anatomy of an adult human being. FIG. 1b shows the periodontal anatomy of an adult human being who suffers from periodontal disease.

The outer surface of the tooth T comprises enamel E and root cementum RC. The dividing line between the enamel E and the root cementum RC is termed the cemento-enamel junction CEJ.

The gums or gingiva G is anatomically divided into two portions—the attached gingiva AG and the free gingiva FG. The alveolar process of the mandible or "alveolar bone" AB is positioned adjacent the root of the tooth T. The periodontal ligament PL connects the tooth T to the alveolar bone AB.

Under normal non-pathological conditions, as illustrated in FIG. 1a, the free gingiva FG lies against the cemento-enamel junction CEJ, thereby fully covering and protecting the root cementum RC. Also, under normal conditions, the periodontal ligament PL forms a AB and the tooth T, thereby holding the tooth firmly in place.

When affected by significant periodontal disease, as illustrated in FIG. 1b, subgingival deposits of microbial plaque and dental calculus C form on the surface of the root cementum RC. The free gingiva FG becomes inflamed and begins to recede away from the tooth T, thereby creating a gap or space GP between the gingiva G and the tooth T. Such gap or space is known as a gingival sulcus or periodontal pocket. If the subgingival plaque or calculus C is not effectively removed, its continued presence will give rise to inflammatory and/or immunological process within the gingiva with a corresponding gradual loss of the periodontal ligament PL and regression of the alveolar bone AB. Such loss of the ligamentous and bony support may ultimately result in loosening and loss of the tooth.

In order to facilitate removal of subgingival plaque or calculus C, the present invention provides a system for visualizing the subgingival tooth surfaces to a greater extent than prior art devices without the need for surgical excision of the surrounding gingiva G. The device of the present invention comprises a dilator projection having an endoscopic looking device formed therein, such as a fiber optic image transmitting means, which is directly insertable into and spreads, via a shield member, the gingival sulcus or periodontal pocket to transmit a visual image of the subgingival tooth surfaces to an eyepiece or video monitor positioned outside the patient's body. The device of the present invention thereby enables the operator to visually guide, monitor and/or assess the efficacy of the plaque or calculus removing treatment. The projection and endoscopic looking device or fiber optic image transmission means formed therein may be incorporated into the body of an instrument used for carrying out subgingival scaling and root planing procedures. Examples of the types of instruments into which the endoscopic looking device or fiber optic means of the present invention may be incorporated include any and all of the instruments typically utilized for performing subgingival scaling and root planing procedures. In particular, specific embodiments of the invention may be incorporated into a hand instrument (e.g., a curette, sickle, chisel, file or hoe) or an ultrasonic or sonic instrument of the type typically utilized to remove subgingival plaque and dental calculus C. Such embodiments of the invention are described in specific detail hereinbelow and show in the accompanying drawings.

Referring now to FIG. 2, there is shown a prior art hand instrument for carrying out subgingival scaling and root planing procedures. Such hand instrument 10 comprises a handle 12, a shank 14, and a working part or blade 16. As is well-known in the art, the working part or blade 16 of the instrument 10 may be in the form of a curette, sickle, hoe, chisel or file and is typically formed of hard material such as carbon steel, stainless steel or tungstdon carbide. The "shank" portion of the instrument is typically continuous with or attached to the working part or blade 16 and is of sufficiently small diameter to be insertable, along with the working part or blade 16, into the subgingival sulcus or pocket.

In carrying out subgingival scaling and root planing procedures deep within the subgingival sulcus or deposit, the commonly used working part or blade 16 is that of a hoe or, as more clearly depicted in FIG. 2a, a curette 28. As illustrated, the curette blade 28 typically comprises a rigid blade member having a generally concave leading surface with two lateral cutting edges. The length and angulation of the shank, as well as the specific dimensions of the curette blade 28, differ depending on the instrument manufacturer and the specific intended application of the instrument.

Although not depicted, it will be recognized by those skilled in the art a multiplicity of other types of instruments can be utilized to remove subgingival deposits of plaque or dental calculus, and may include, but by no means are limited to, ultrasonic instruments, sonic instruments, and/or rotating instruments. Similar to the aforementioned discussion regarding hand instruments, instruments in each of the aforementioned classes typically comprise an elongated handle portion having a treatment head or tip which is sized and configured for insertion into the subgingival sulcus or pocket, the latter being operative to remove the target plaque/calculus.

Notwithstanding the general effectiveness of each of the aforementioned class of prior art tools, of which FIGS. 2 and 2a are merely representative, there exists a need in the art for endoscopically viewing the subgingival tooth surfaces and/or subgingival tissues of the periodontium during various treatment procedures directed at the subgingival tooth surfaces and/or subgingival tissues. Among the attempts made and the prior art to address and alleviate such needs, include those endoscopic methods and devices for subgingival dental procedures disclosed in U.S. Pat. No. 5,230,621 and 5,328,365 entitled, respectively, Endoscopic Method And Device For Subgingival Dental Procedures, and System And Method For Endoscopic Subgingival Dental Procedures, both to Jacoby, the teachings of which are expressly incorporated herein by reference.

Such prior art devices, however, fail to provide a sufficiently wide enough field of vision due to the orientation of the distal end of the endoscope formed thereon, which serves to depict more of the dental instrumentation, as opposed to the tooth surface sought to be viewed. Additionally, due to the close proximity of the distal-most end of the endoscopic viewing apparatus relative the working part or blade of such dental instrumentation, the depth of vision is distorted and does not provide the operator with the optimal depth of vision necessary to fully evaluate and visually asses subgingival plaque/calculus removal procedures.

Figure 3:
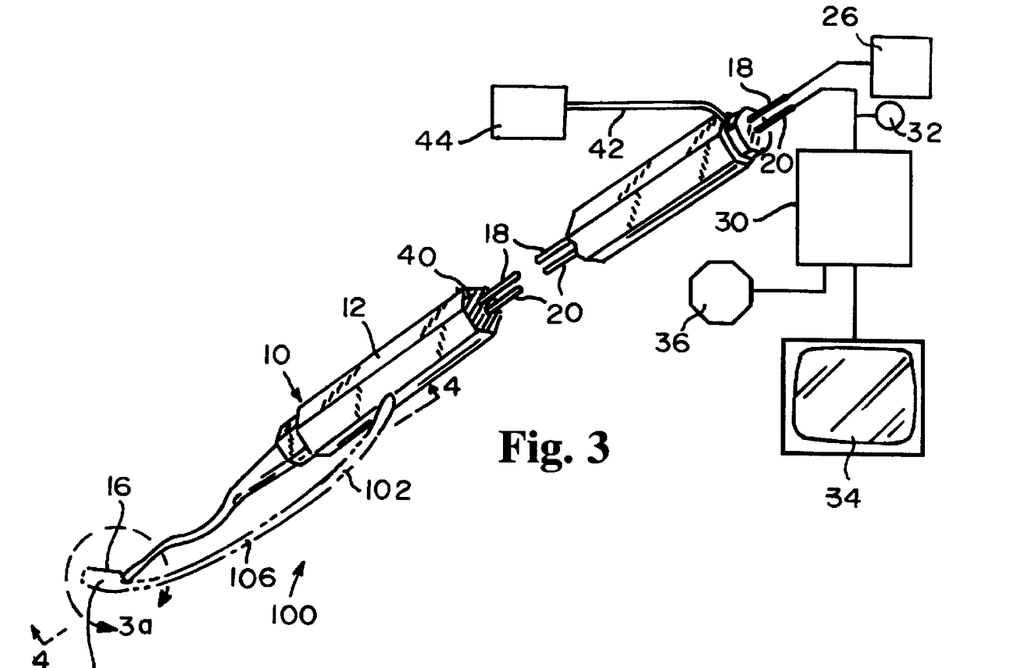
FIG. 3 is a perspective view of the dental instrument shown in FIG. 2 having a gingival tissue projection with endoscopic viewing apparatus formed thereon, the latter constructed in accordance to a preferred embodiment of the present invention.

As perspectively illustrated in FIG. 3, there is shown an improved dental endoscopic system 100 that provides a substantially greater field of vision and depth of vision than prior art devices that, as a consequence, greatly enhances the ability of the operator of such instrument to visually assess subgingival plaque/calculus removal procedures. As illustrated, the invention 100 comprises the combination of a conventional dental instrument 10 utilized to remove plaque and calculus from subgingival tooth surfaces that further has formed thereon a dilator projection 102, the latter having an endoscopic viewing apparatus (not shown) formed therewithin that permits enhanced visualization and visual assessment of target tooth surfaces upon which subgingival plaque/calculus removal procedures are performed. As illustrated, the dilator projection 102 comprises a thin, flat shield member 104 oriented and secured in close proximity towards the working part or blade 16 of the dental instrument 10, discussed more fully below in relation to FIGS. 3a and 3a'. Extending rearwardly from the shield member 104 is an arcuate shank or arm 106, that connects the shield member with the handle portion 12 of the dental instrument 10.

Similar to prior art dental endoscopic viewing systems, there is disposed within such dental instrument 10 a first optical fiber or bundle 18 and a second optical fiber group or bundle 20 that extends longitudinally through the handle portion 12. As will be recognized by those skilled in the art, the first optical fiber bundle 18 comprises light transmitting optical fibers whereas the second optical fiber bundle 20, comprises image transmitting fibers.

The proximal end of the first (illuminating) fiber bundle 18 is connectable to an external light source 26 such that illuminating light may be conveyed and transported by the first optical fiber bundle 18 through the handle portion 12 of the instrument 10.

Similarly, the proximal end of the second (image transmitting) optical fiber bundle 20 is operatively connected to a solid state video-imaging device 30 such as a video monitor or television monitor and/or an eyepiece 32. As will be recognized, the eyepiece 32 may comprise any suitable optical eyepiece for receiving and viewing an optical image transmitted by the second image transmitting fiber bundle 20.

The imaging device 30 may comprise any presently or hereafter known video signal processing device capable of accepting visual image information transmitted through the second image transmitting optical fiber bundle 20 and conveying such visual image information to a video signal. The video signal generated by the imaging device 30 may then be shown on a video monitor 36 connected to such imaging device 30. Additionally or alternatively, the video signal generated by the imaging device 30 may be recorded on a recording device 34 operatively connected to such imaging device 30 or image-viewing device.

Figure 4:
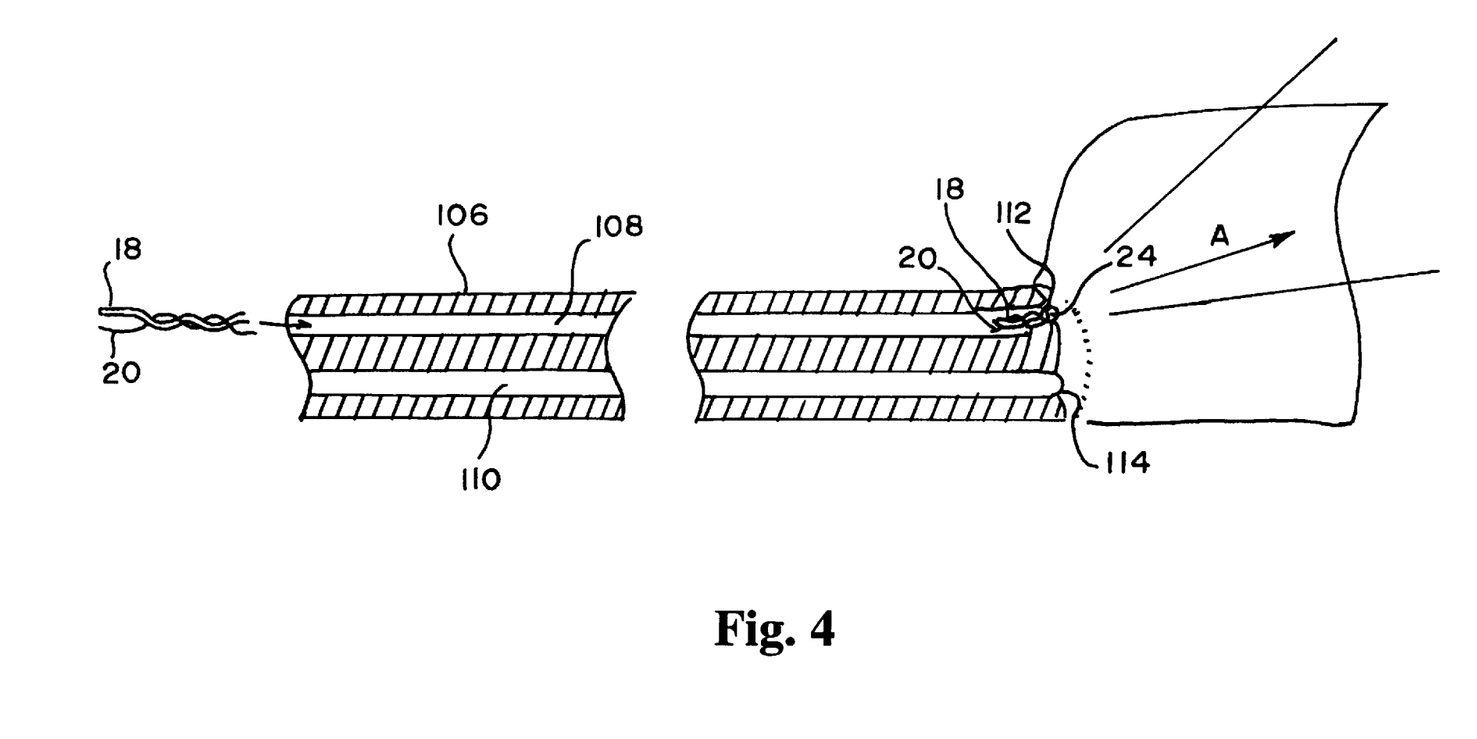
FIG. 4 is a cross-sectional view taken along lines 4—4 of FIG. 3.

The distal portions of the first 18 and second 20 optical fiber bundles extend from the handle portion 12 of the instrument 10 and through the arcuate shank portion 106 formed upon the projection member 102. In this regard, and as shown in FIG. 4, at least one 108 and preferably two 110 dedicated lumens are formed within the arm or shank portion 106 of the projection 102 that extend longitudinally therethrough. Preferably, the optical fibers of the first 18 and second 20 optical fiber bundles may be combined, fused, intermingled, juxtapositioned or otherwise arranged as a single group or single bundle of fibers wherein both the image transmitting and illuminating fibers are disposed. As a consequence, only one of the lumens 108, 110 formed within the shank portion 106 of the projection 102 will be occupied therewith, leaving a second lumen available to perform other utility functions, discussed more fully below.

Figure 3A:
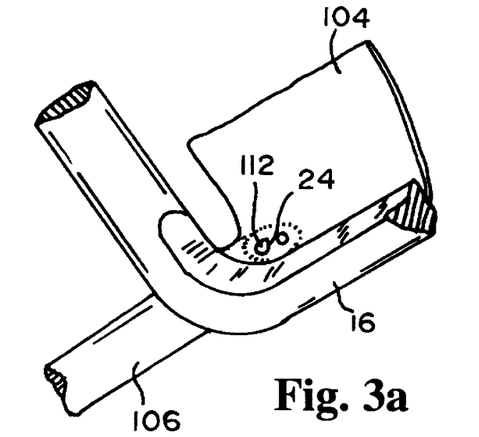
FIG. 3a is an enlarged side perspective view of the distal portions of the working part of the instrument and gingival tissue dilator projection with viewing apparatus shown in FIG. 3.

As will be recognized by those skilled in the art, the first 18 and second 20 optical fiber bundles are attached to and terminate within a distal illuminating/image receiving apparatus or optical head 24, the latter being selectively positioned upon an aperture 112 formed upon the distal-most end of the shank, more clearly illustrated in FIGS. 3 and 3a'.

Advantageously, by selectively positioning the optical head 24 apart from the working part or blade 16 of the dental instrument, there is provided a substantially greater field of view of the region of the tooth surface upon which the working part of the dental instrument is operative to remove plaque and/or calculus deposits.

Additionally, by virtue of the proximity of the optical head 24 as formed upon the distal-most end of the shank portion 106 of the projection 102, a greater depth of vision is also provided which enables the operator to more accurately assess the severity of plaque and/or calculus deposits being treated and to guide the use of the instrument 10 in a manner which effectively removes the entirety of such plaque or calculus deposits than prior endoscopic systems and techniques. As will likewise be appreciated by those skilled in the art, the visualization of the tooth surface sought to be observed may further be enhanced by forming the lumen 108 within the shank 106, and particularly the aperture formed thereby at the distal-most end thereof such that the optical head 24 is caused to cant or tilt selectively upward as indicated by the letter "A" in FIG. 4. As a result, the working part 16 or the instrument is deleted from the field of vision so that the field of vision of the tooth surfaces sought to be visualized are maximized.

To further facilitate and maximize such viewing field, the shield portion 104 is provided to dilate or spread the gingiva away from the adjacent tooth surfaces upon which the working part or blade is operative to remove plaque therefrom. In this regard, such shield 104 serves to create a space between the gingiva and the tooth surfaces such that the endoscopic viewing apparatus. More particularly the optical head 24 (i.e., the fiber optic bundles, and optical head 24 formed at the distal end thereof) may openly view the tooth surfaces as desired. Such shield 104 is effective in facilitating use of the endoscopic viewing apparatus of the present invention even in cases where the gingiva is pressing against or budding the adjacent tooth surfaces. Advantageously, however, unlike prior art devices, by forming the shield upon the distal-most end of the shank, and adjacent to the working part of the dental instrument, and forming the optical head 24 upon the distal-most end of the shank 106, there is thus provided a vantage point that achieves an optimal field of vision not yet achieved in the prior art.

To further facilitate the functionality of the endoscopic viewing system of the present invention, there may further optionally be provided one or more lumens such as 110, extending longitudinally within the shank portion of the projection 102 and terminating at the distal-most end thereof, the latter defining an aperture 114 so that the working part of the dental instrument may be accessed. As will be understood, such lumen 110 may comprise an optional infusion fluid lumen. Such optional infusion fluid lumen may be connected at its proximal end, by way of tubing 42 to a source or pressurized infusion fluid or a pump 44. Such optional infusion fluid lumen is fluidly connected to one or more infusion fluid outflow apertures or ports formed in the distal portion of the shank and/or in the blade portion of the instrument.

Such passage of water or other fluid may be utilized to accomplish periodic continuous washing or lavage of the periodontal pocket PP during operative use of the instrument, thereby clearing blood and debris from the visualized field ahead of the working part or blade of the instrument. Such washing or lavage within the periodontal pocket will facilitate the endoscopic visualization of the subgingival tooth surfaces as desired, as well as causing distension of the pocket by insufflation with the infused fluid. Such lumen and ports may alternately be attached to a suction source for aspiration fluid and/or debris out of the periodontal pocket.

In some embodiments, an optional additional (i.e., apart from the infusion lumen) aspiration lumen (not shown) attachable to a suction source or external aspiration device may also be formed longitudinally through the instrument to effect suction or aspiration of fluid and/or debris from the periodontal pocket during operation of the device.

Figure 5:
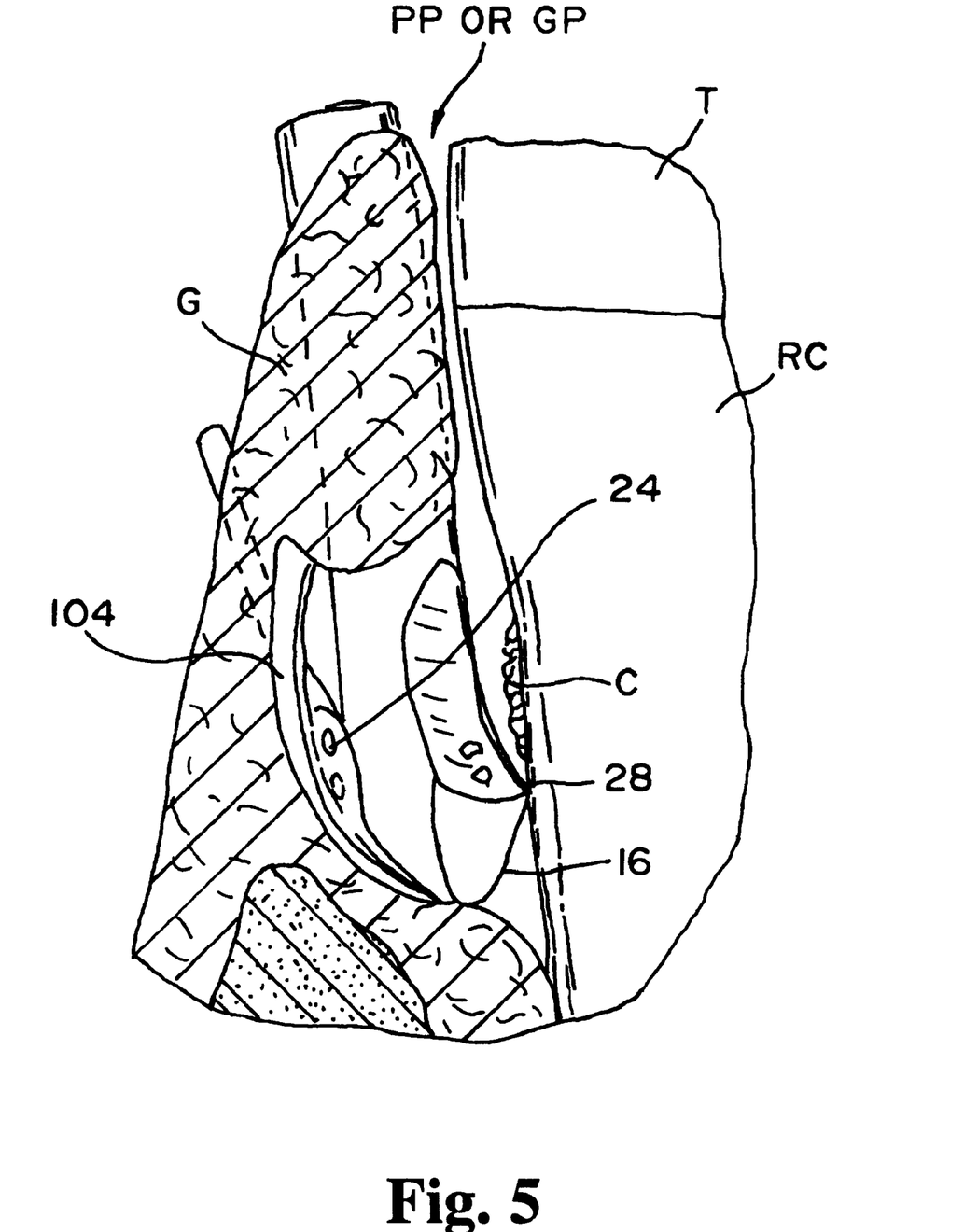
FIG. 5 is a schematic diagram of a portion of the human dental anatomy showing the instrument of FIG. 3 and its operative disposition within the periodontal pocket or crevice.

With respect to the operation of the endoscopic viewing system of the present invention, there is shown in FIG. 5 a schematic diagram depicting a portion of the human dental anatomy showing the instrument depicted in FIG. 3 in its operative disposition within the periodontal pocket or crevice. As shown, the shield portion 104 of the dilator projection 102 extends in a general proximal direction from one side of the working part or blade 16 of the instrument 10. Such shield 106 is preferably shaped in a slightly rounded or blunt configuration so as to minimize or avoid traumatization of the gingiva G. The shield 104 is preferably sized and configured to spread and hold the gingiva G away from the tooth surface over a region or area ahead of the leading edge of the working part of the blade 16, thereby preventing the gingiva G from interfering with visualization of the tooth surface within such region or area ahead of the working part or blade 16 formed upon the distal end of the shank 104.

As shown, the optical head 24 formed upon the distal end of the shank 106 is positioned in relation to the shield 104 such that the shield protects the optical head, thereby preventing direct contact between the gingiva G and the optical head 24. Furthermore, due to the advantageous proximity of the optical head 24 relative the working part or blade 16 of the dental instrument, namely, set further back and tilted at an angle to view the tooth surfaces over and above the surface upon which the working part or blade 16 is operative, there is thus provided the enhanced visualization of such surfaces, as assessed above.

Although the working part or blade 16 of the instrument depicted in FIG. 5 comprises a curette blade 28, it should be understood that any other type of working part or blade presently or hereafter used to scrape or abrade subgingival tooth surfaces, including, but not limited to those known in the art as hoes, sickles, chisels or files, may be utilized. It will additionally be appreciated that, in accordance with the present invention, the projection with endoscopic viewing apparatus formed therein may be incorporated into any type of hand, ultrasonic or rotating instrument usable for the purposes of effecting subgingival scraping procedures (e.g., scaling and root planing) procedures.

The invention has been described herein with reference to presently preferred embodiments of the device. None of the descriptions or examples set forth herein are intended to limit the scope of the invention. In fact, it is expected that persons of skill in the art will recognize numerous alternatives, additions and modifications which may be applied to the specific embodiments and examples described herein. It is intended that all such alternatives, additions and modifications be included within the scope of the present invention as defined by the following claims and the equivalence thereof.

What is claimed is:

1. A dental instrument for removing deposits of dental plaque and calculus from subgingival tooth surfaces under endoscopic visualization comprising:
    a) an elongate handpiece having proximal and distal ends, said proximal end defining a handle, said handpiece having a working part extending from the distal end thereof, said working part being sized and configured to be insertable between the free gingiva and the subgingival tooth surfaces and usable to remove plaque and calculus deposits from said subgingival tooth surfaces;
    b) an elongate projection member having proximal and distal ends, said proximal end of said projection member being formed upon said handle of said handpiece such that said projection member extends distally toward said working part of said handpiece, said projection member having a shield member formed on the distal end thereof for spreading and holding the gingiva from said subgingival tooth surfaces from which said plaque and calculus are sought to be removed; and
    c) an endoscopic viewing apparatus extending longitudinally through said handle of said handpiece and through said projection member, said endoscopic viewing apparatus being operative to transmit light upon and transmit optical images from the subgingival tooth surfaces adjacent the working part of said instrument.

2. The dental instrument of claim 1 wherein said working part of said handpiece is operative to remove said deposits of dental plaque and calculus via means selected from the group consisting of ultrasonic vibration, sonic vibration and rotational scraping.

3. The dental instrument of claim 1 wherein said working part of said handpiece comprises an elongate member sized and configured to scrape deposits from said subgingival tooth surfaces.

4. The dental instrument of claim 3 wherein said elongate member is selected from the group consisting of a curette blade, a hoe, a sickle, and a file.

5. The dental instrument of claim 1 wherein said projection further comprises an arcuate shank portion extending from said handle of said handpiece to said shield member, said shank having at least one lumen disposed therein for receiving said endoscopic viewing apparatus.

6. The dental instrument of claim 5 wherein said at least one lumen formed within said shank of said projection member defines an aperture at the distal-most end thereof and proximal said shield member, said aperture being operative to cant the distal end of said endoscopic viewing apparatus.

7. The dental instrument of claim 6 wherein said aperture formed upon the distal end of said shank is formed to orient the distal end of said endoscopic viewing apparatus such that said distal end of said endoscopic viewing apparatus illuminates and transmits images of subgingival tooth surfaces substantially above the working part of said handpiece.

8. The dental instrument of claim 1 wherein said handle portion of said handpiece and said projection further include at least one additional lumen extending therethrough, said at least one additional lumen defining an aperture located upon the distal portion of said projection.

9. The dental instrument of claim 8 wherein at least one additional lumen and aperture formed upon the projection thereby is operative to permit infusion of fluid therethrough.

10. The dental instrument of claim 8 wherein said at least one additional lumen and aperture formed upon said projection thereby is operative to permit aspiration of fluid therethrough.

11. The dental instrument of claim 1 wherein said endoscopic viewing apparatus comprises:
    a) at least one bundle of optical fibers for transmitting light, said bundle having a proximal end which is connectable to a light source, said bundle of optical fibers for transmitting light extending distally from said proximal end thereof to at least one illumination outlet port located adjacent to the working part of said instrument; and
    b) at least one bundle of elongate optical fibers for transmitting an image, said at least one bundle of image transmission optical fibers having a proximal end which is connectable to an external image viewing apparatus, said image transmission optical fiber bundle extended distally from said proximal end thereof to at least one optical image receiving port.

12. The dental instrument of claim 11 wherein said optical fiber bundle for transmitting light and said optical fiber bundle for transmitting an optical image are arranged as a single group such that in use, said optical fiber group extends through a single dedicated lumen extending from said handle portion of said handpiece and through said projection extending distally therefrom.

13. The dental instrument of claim 11 wherein said illumination outport comprises a lens.

14. The dental instrument of claim 11 wherein said optical imagery receiving port comprises a lens.

15. A projection member for facilitating the endoscopic visualization of procedures for removing deposits of dental plaque and calculus from the working part of a dental instrument comprising:

a) an elongate shank having proximal and distal ends, said proximal end of said shank being positionable upon said dental instrument such that said distal end of said shank is oriented toward said working part of said instrument;

b) a shield member formed upon said distal end of said shank, said shield being sized and configured to widen portions of the gingival sulcus by separating the gingival tissue away from the subgingival tooth surface from which said plaque and calculus are remove; and c) at least one lumen extending along the length of said shank for receiving any endoscopic viewing apparatus, said at least one lumen defining an aperture at the distal end of said shank that is sized and configured to selectively cant the distal end of said endoscopic viewing apparatus such that said endoscopic viewing apparatus is caused to produce a field of vision of said subgingival tooth surfaces that substantially omits visualization of the working part of said dental instrument.

16. The projection of claim 15 wherein said projection is mounted upon a dental instrument selected from the group consisting of hand instruments, ultrasonic instruments, sonic instruments and rotational instruments.

17. The projection of claim 15 wherein said shield member is welded to a portion of said working part of said instrument.

18. The projection of claim 15 wherein said shield portion of said projection is configured and oriented to align with a abut a portion of said working part of said dental instrument.

19. The projection of claim 15 wherein said projection further comprises at least one additional lumen formed within said shank portion, said at least one additional lumen defining at least one additional aperture upon the distal end of said shank.

20. The projection of claim 19 wherein said at least one additional lumen comprises an infusion lumen for permitting infusion of fluid therethrough.

21. The projection of claim 19 wherein said at least one additional lumen comprises an aspiration lumen to permit aspiration of fluid therethrough.

* * * * *